(12) United States Patent
Rearden

(10) Patent No.: US 6,245,522 B1
(45) Date of Patent: Jun. 12, 2001

(54) MASTER MOLECULAR RHEOSTAT SWITCH FOR CELL SIGNALING

(75) Inventor: Ann Rearden, Rancho Santa Fe, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/276,851

(22) Filed: Mar. 26, 1999

(51) Int. Cl.[7] .................................................. G01N 33/53
(52) U.S. Cl. .............................. 435/7.23; 435/4; 435/7.1; 435/7.9

(58) Field of Search .................................. 435/4, 7.1, 7.9, 435/7.23

(56) References Cited

U.S. PATENT DOCUMENTS 5,552,529  9/1996  Rearden ............................... 530/380

*Primary Examiner*—Sheela Huff
(74) *Attorney, Agent, or Firm*—Gray Cary Ware & Freidenrich LLP; Lisa A. Haile

(57) ABSTRACT

Methods of detecting cell signaling disorders associated with PINCH and ILK, including cell proliferative disorders such as breast cancer are disclosed. Methods of treating and diagnosing disease and disorders associated with PINCH and ILK cell signaling are also disclosed.

8 Claims, 2 Drawing Sheets

Table 1. Results with Human Breast Specimens

| Case | DIAGNOSIS | PINCH | ILK | erbB-2 | cyclin D1 | ER/PR | DNA Index | S phase | Nodes |
|---|---|---|---|---|---|---|---|---|---|
| 1 | Normal breast | normal | normal | negative | normal | n.d.** | n.d. | n.d. | n.d. |
| 2 | Normal breast | normal | normal | negative | normal | n.d. | n.d. | n.d. | n.d. |
| 3 | Primary ductal carcinoma | increased | increased | negative | normal | positive | 1.0 | 4.8 | n.d. |
| 4 | Primary ductal carcinoma | increased | increased | negative | normal | negative | 1.4 | 21.5 | positive |
| 5 | Primary ductal carcinoma | increased | increased | negative | increased | negative | n.d. | n.d. | negative |
| 6 | Primary ductal carcinoma, neuroendocrine | increased | increased | positive | increased | negative | 1.6 | 8.8 | negative |
| 7 | Metastatic ductal carcinoma | increased | increased | positive | increased | negative | n.d. | n.d. | positive |
| 8 | Primary lobular carcinoma | increased | increased | negative | increased | positive | 1.8 | 9.2 | n.d. |

* ER/PR=estrogen and progesterone receptors
** n.d.=not done

FIG. 1

```
                                                                          60
ATG GCC AAC GCC CTG GCC AGC GCC ACT TGC GAG CGC TGC AAG GGC GGT TTT GCG CCC GCT
Met Ala Asn Ala Leu Ala Ser Ala Thr Cys Glu Arg Cys Lys Gly Gly Phe Ala Pro Ala

120
GAG AAG ATC GTG AAC AGT AAT GGG GAG CTG TAC CAT GAG CAG TGT TTC GTG TGC GCT CAG
Glu Lys Ile Val Asn Ser Asn Gly Glu Leu Tyr His Glu Gln Cys Phe Val Cys Ala Gln

180
TGC TTC CAG CAG TTC CCA GAA GGA CTC TTC TAT GAG TTT GAA GGA AGA AAG TAC TGT GAA
Cys Phe Gln Gln Phe Pro Glu Gly Leu Phe Tyr Glu Phe Glu Gly Arg Lys Tyr Cys Glu

240
CAT GAC TTT CAG ATG CTC TTT GCC CCT TGC TGT CAT CAG TGT GGT GAA TTC ATC ATT GGC
His Asp Phe Gln Met Leu Phe Ala Pro Cys Cys His Gln Cys Gly Glu Phe Ile Ile Gly
                                       ◆                                 300
CGA GTT ATC AAA GCC ATG AAT AAC AGC TGG CAT CCG GAG TGC TTC CGC TGT GAC CTC TGC
Arg Val Ile Lys Alg Met Asn Asn Ser Trp His Pro Glu Cys Phe Arg Cys Asp Leu Cys

*******360
CAG GAA GTT CTG GCA GAT ATC GGG TTT GTC AAG AAT GCT GGG AGA CAC CTG TGT CGC CCC
Gln Glu Val Leu Ala Asp Ile Gly Phe Val Lys Asn Ala Gly Arg His Leu Cys Arg Pro

*******                                       ****************** 420
TGT CAT AAT CGT GAG AAA GCC AGA GGC CTT GGG AAA TAC ATC TGC CAG AAA TGC CAT GCT
Cys His Asn Arg Glu Lys Ala Arg Gly Leu Gly Lys Tyr Ile Cys Gln Lys Cys His Ala

------------------------------  480
ATC ATC GAT GAG CAG CCT CTG ATA TTC AAG AAC GAC CCC TAC CAT CCA GAC CAT TTC AAC
Ile Ile Asp Glu Gln Pro Leu Ile Phe Lys Asn Asp Pro Tyr His Pro Asp His Phe Asn

540
TGC GCC AAC TGC GGG AAG GAG CTG ACT GCC GAT GCA CGG GAG CTG AAA GGG GAG CTA TAC
Cys Ala Asn Cys Gly Lys Glu Leu Thr Ala Asp Ala Arg Glu Leu Lys Gly Glu Leu Tyr

******************                                                       600
TGC CTC CCA TGC CAT GAT AAA ATG GGG GTC CCC ATC TGT GGT GCT TGC CGA CGG CCC ATC
Cys Leu Pro Cys His Asp Lys Met Gly Val Pro Ile Cys Gly Ala Cys Arg Arg Pro Ile

660
GAA GGG CGC GTG GTG AAC GCT ATG GGC AAG CAG TGG CAT GTG GAG CAT TTT GTT TGT GCC
Glu Gly Arg Val Val Asn Ala Met Gly Lys Gln Trp His Val Glu His Phe Val Cys Ala

720
AAG TGT GAG AAA CCC TTT CTT GGA CAT CGC CAT TAT GAG AGG AAA GGC CTG GCA TAT TGT
Lys Cys Glu Lys Pro Phe Leu Gly His Arg His Tyr Glu Arg Lys Gly Leu Ala Tyr Cys

780
GAA ACT CAC TAT AAC CAG CTA TTT GGT GAT GTT TGC TTC CAC TGC AAT CGT GTT ATA GAA
Glu Thr His Tyr Asn Gln Leu Phe Gly Asp Val Cys Phe His Cys Asn Arg Val Ile Glu

840
GGT GAT GTG GTC TCT GCT CTT AAT AAG GCC TGG TGC GTG AAC TGC TTT GCC TGT TCT ACC
Gly Asp Val Val Ser Ala Leu Asn Lys Ala Trp Cys Val Asn Cys Phe Ala Cys Ser Thr

900
TGC AAC ACT AAA TTA ACA CTC AAG AAT AAG TTT GTG GAG TTT GAC ATG AAG CCA GTC TGT
Cys Asn Thr Lys Leu Thr Leu Lys Asn Lys Phe Val Glu Phe Asp Met Lys Pro Val Cys

AAG AAG TGC TAT GAG ATT TCC ATT GGA GCT GAA GAA AAG ACT
Lys Lys Cys Tyr Glu Ile Ser Ile Gly Ala Glu Glu Lys Thr
```

FIG. 2

MASTER MOLECULAR RHEOSTAT SWITCH FOR CELL SIGNALING

FIELD OF THE INVENTION

This invention relates to cellular regulation, and more particularly to cell signaling in cell proliferative disorders.

BACKGROUND OF THE INVENTION

PINCH (Particularly Interesting New Cys-His protein) is a LIM-only protein consisting primarily of five LIM domains. The LIM motif, recognized in 1990 in the lin-11, isl-1 and mec 3 proteins, specifies a double zinc finger domain which has been shown to participate in protein-protein interactions. Within the LIM family PINCH has the largest number of LIM domains (five), giving rise to ten zinc fingers.

The function of LIM domain proteins as adapters and modifiers in protein interactions has been reviewed recently. PINCH likely functions as an adapter protein for signal transduction. Adapter molecules such as PINCH can control the location, assembly and function of signaling networks, and may be constitutively-anchored to a particular subcellular localization or may be recruited to a signaling site. Because PINCH is associated with $\beta 1$ integrin, a protein localized to the plasma membrane, it is reasonable to assume that PINCH functions as an anchoring adapter protein, targeting signaling components to sites of signal transduction at the cell membrane.

The PINCH signaling complex also contains the integrin-linked kinase (ILK), a serine-threonine kinase that associates with the cytoplasmic tails of integrins $\beta 1$ and $\beta 3$. ILK is involved in integrin-mediated signaling as well as in the $\beta$-catenin/LEF-1 signaling pathway, participating in the complex signaling interactions that occur at cell-matrix and cell-cell junctions. ILK may function in crosstalk between cell-matrix and cell-cell junctions and also with components of the Wnt signaling pathway.

ILK has been shown to have oncogenic properties. ILK-over expressing cells are tumorigenic in nude mice. The mechanisms by which ILK up regulation leads to a transformed phenotype are as yet poorly understood, but the available information points to effects on the nucleus. ILK over expression leads to up regulation of specific cell-cycle associated proteins and to the translocation of $\beta$-catenin from the cell membrane to the nucleus where it forms a complex with the transcription factor LEF-1. Because ILK over expression in cultured epithelial cells leads to enhanced fibronectin matrix assembly (a feature of mesenchymal cells), it is possible that ILK over expression in epithelial cells is associated with activation of mesenchymal gene expression.

SUMMARY OF THE INVENTION

The present invention provides a method of inhibiting a cell signaling disorder comprising administering to a subject a composition containing an agent which regulates a PINCH polypeptide or PINCH expression. The method is useful in inhibiting a cell proliferative disorder.

In one embodiment the invention provides a method of diagnosing a cell proliferative disorder in a subject associated with PINCH by determining the level of PINCH in the sample and comparing the level of PINCH in the sample to the level of PINCH in a standard sample, wherein an elevated level of PINCH is indicative of a cell proliferative disorder.

In another embodiment, the invention provides a method of ameliorating a cell proliferative disorder associated with PINCH, comprising treating a subject having the disorder with an agent that regulates PINCH activity or expression. The agent can be an antibody, polypeptide, antisense molecule or chemical.

In a further embodiment, the invention provides a method for identifying a compound which modulates cell proliferation, by contacting a sample containing PINCH polypeptide with a compound suspected of having PINCH modulating activity and detecting an effect on cell proliferation.

The invention also provides a method for identifying a cell proliferative disorder in a subject comprising, quantifying the expression of PINCH, ILK, or a combination thereof and correlating the level of expression with the presence of a cell proliferative disorder, wherein an elevated level of PINCH is indicative of a cell proliferative disorder and wherein an elevated level of ILK is indicative of a metastatic cell proliferative disorder.

In another embodiment, the invention provides a method for detecting a cell proliferative disorder in a subject, comprising, quantifying expression of polynucleotides encoding PINCH, ILK or a combination thereof wherein the polynucleotide level determines the presence of the cell proliferative disorder.

In yet another embodiment, the invention provides a method for detecting a cell proliferative disorder in a subject comprising quantifying PINCH polypeptide, ILK polypeptide or a combination thereof, wherein the levels of PINCH and ILK when compared to a standard sample are indicative of the presence of a cell proliferative disorder.

In yet another embodiment the invention provides a method of diagnosing breast cancer in a subject comprising detecting PINCH in cells isolated from the subject, wherein an elevated amount of PINCH when compared to a standard sample is indicative of a breast caner.

Furthermore, the invention provides a method of diagnosing a metastatic breast cancer in a subject comprising detecting PINCH and ILK in cells isolated from the subject, wherein in an elevated amount of PINCH and ILK compared to a standard sample is indicative of a metastatic breast cancer.

The invention also provides a method of determining the prognosis of a patient having a cell proliferative disorder comprising determining the level of PINCH and ILK in cells of a patient and correlating the level with prognosis of the patient.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a table representing a spectrum of breast cancer diagnoses and varied expression of known prognostic indicators.

FIG. 2 depicts the nucleic acid sequence (SEQ ID NO:1) and the corresponding amino acid sequence (SEQ ID NO:2) of PINCH.

DETAILED DESCRIPTION OF THE INVENTION

The present invention relates to a method of detecting, diagnosing, and treating signal transduction disorders, such as those related to a cell proliferative disorder, neoplasm or cancer using PINCH polypeptides, antibodies to PINCH polypeptides, and PINCH polynucleotides, including antisense molecules, ribozymes and complementary polynucleotides.

In its broadest sense, the present invention allows the detection of any PINCH-associated disorder in any organ, tissue, or cell, where the target polynucleotide sequence or polypeptide sequence encodes a PINCH polypeptide or is a PINCH polynucleotide. Thus, the target polynucleotide sequence may be, for example, a mutant polynucleotide, a restriction fragment length polymorphism (RFLP), a polynucleotide deletion, a polynucleotide substitution, or any other mammalian nucleic acid sequence of interest encoding a PINCH polypeptide. Additionally, the present invention allows for the detection of PINCH polypeptides or fragments thereof. The PINCH polypeptides are described in U.S. Pat. No. 5,552,529 the disclosure of which is incorporated herein by reference.

As used herein, the term "nucleic acid," "polynucleotide," "oligonucleotide" or "nucleic acid sequence" refers to a polymer of deoxyribonucleotides or ribonucleotides, in the form of a separate fragment or as a component of a larger construct. For example, nucleic acids can be assembled from cDNA fragments or from polynucleotides to generate a synthetic gene which is capable of being expressed in a recombinant transcriptional unit. Oligonucleotide or nucleic acid sequences of the invention include DNA, RNA, and cDNA sequences.

A "promoter" is a minimal DNA sequence sufficient to direct transcription of a DNA sequence to which it is operably linked. A "promoter" also includes promoter elements sufficient for promoter-dependent gene expression controllable for cell-type specific expression, tissue-specific expression, or inducible by external signals or agents; such elements may be located in the 5' or 3' regions of the native gene.

The term "operably associated" refers to functional linkage between the regulatory (e.g. promoter) sequence and the nucleic acid regulated by the regulatory sequence. The operably linked regulatory sequence controls the expression of the product. The regulatory sequence may be heterologous to the desired gene sequence.

A "vector" is any compound or formulation, biological or chemical, that facilitates transformation or transfection of a target cell with a polynucleotide of interest, for example antisense oligonucleotides. Exemplary biological vectors include viruses, particularly attenuated and/or replication-deficient viruses. Exemplary chemical vectors include lipid complexes and DNA constructs.

To "inhibit" or "inhibiting" activity is to reduce that activity a measurable amount, preferably a reduction of at least 30% or more. Where there are multiple different activities that may be inhibited (for example, antisense molecules that bind polynucleotides encoding PINCH or ILK may have the ability to reduce expression of the PINCH or ILK protein, the reduction of any single activity (with or without the other activities) is sufficient to fall within the scope of this definition.

To "specifically bind" is to preferably hybridize to a particular polynucleotide species. The specificity of the hybridization can be modified and determined by standard molecular assays known to those skilled in the art.

A "suppressive-effective" amount is that amount of the construct, for example an antisense construct, administered in an amount sufficient to suppress the expression of the target, e.g., inhibit translation of mRNA, by at least 75% of the normal expression, and preferably by at least 90%. The effectiveness of the construct can be determined phenotypically or by standard Northern blot analysis or immunohistochemically, for example. Other standard nucleic acid detection techniques or alternatively immunodiagnostic techniques will be known to those of skill in the art (e.g., Western or Northwestern blot analysis).

Diagnostic Techniques

The invention provides a method for detecting a cell signaling disorder associated with PINCH or a cell proliferative disorder associated with PINCH in a tissue of a subject, comprising contacting a target cellular component suspected of expressing PINCH or having a PINCH associated disorder, with a reagent which binds to the component. The target cell component can be nucleic acid, such as DNA or RNA, or protein. When the component is nucleic acid, the reagent is a polynucleotide probe or PCR primer. When the cell component is a polypeptide, the reagent is an antibody probe. The probes can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the antibody, or will be able to ascertain such, using routine experimentation.

For purposes of the invention, an antibody or nucleic acid probe specific for PINCH may be used to detect the presence of PINCH polypeptide (using antibody) or polynucleotide (using nucleic acid probe) in biological fluids or tissues. Oligonucleotide primers based on any coding sequence region in the PINCH sequence are useful for amplifying polynucleotides encoding PINCH, for example by PCR. Any specimen containing a detectable amount of polynucleotide or antigen can be used. A preferred sample of this invention is breast tissue. Alternatively, biological fluids such as blood may be used which may contain cells indicative of a PINCH-associated cell proliferative disorder. Preferably the subject is human.

A number of techniques known to those skilled in the art may be used to detect polynucleotides encoding PINCH. For example, RNAse protection assays may be used if RNA is the polynucleotide obtained from the sample. In this procedure, a labeled antisense RNA probe is hybridized to the complementary polynucleotide in the sample. The remaining unhybridized single-stranded probe is degraded by ribonuclease treatment. The hybridized, double stranded probe is protected from RNAse digestion. After an appropriate time, the products of the digestion reaction are collected and analyzed on a gel (see for example Ausubel et al., CURRENT PROTOCOLS IN MOLECULAR BIOLOGY, section 4.7.1 (1987)). As used herein, "RNA probe" refers to a polynucleotide capable of hybridizing to RNA in a sample of interest. Those skilled in the art will be able to identify and modify the RNAse protection assay specific to the polynucleotide to be measured, for example, probe specificity may be altered, hybridization temperatures, quantity of nucleic acid as well as other variables known to those skilled in the art. Additionally, a number of commercial kits are available, for example, RiboQuantTM Multi-Probe RNAse Protection Assay System (Pharmingen, Inc., San Diego, Calif.).

Additionally, detection of a polynucleotide encoding PINCH may be performed by standard methods such as size fractionating the nucleic acid. Methods of size fractionating the DNA and RNA are well known to those of skill in the art, such as by gel electrophoresis, including polyacrylamide gel electrophoresis (PAGE). For example, the gel may be a denaturing 7 M or 8 M urea-polyacrylamide-formamide gel. Size fractionating the nucleic acid may also be accomplished by chromatographic methods known to those of skill in the art.

The detection of polynucleotides may optionally be performed by using radioactively labeled probes. Any radioactive label may be employed which provides an adequate signal. Other labels include ligands, which can serve as a specific binding pair member for a labeled ligand, and the like. The labeled preparations are used to probe for a polynucleotide by the Southern or Northern hybridization techniques, for example. Nucleotides obtained from samples are transferred to filters that bind polynucleotides. After exposure to the labeled polynucleotide probe, which will hybridize to nucleotide fragments containing target nucleic acid sequences, the binding of the radioactive probe to target nucleic acid fragments is identified by autoradiography (see *Genetic Engineering*, 1, ed. Robert Williamson, Academic Press (1981), pp. 72–81). The particular hybridization technique is not essential to the invention. Hybridization techniques are well known or easily ascertained by one of ordinary skill in the art. For example, RNA is separated on a gel transferred to nitrocellulose and probed with complementary DNA to the sequence of interest. The complementary probe may be labeled radioactively, chemically etc. Hybridization of the probe is indicative of the presence of the polynucleotide of interest. The relative intensity of a reporter attached to the probe, for example a radionucleotide, can be indicative of the amount of PINCH polynucleotide present in the sample. As improvements are made in hybridization techniques, they can readily be applied in the method of the invention.

The polynucleotides encoding a PINCH or ILK polypeptide may be amplified before detecting. The term "amplified" refers to the process of making multiple copies of the nucleic acid from a single polynucleotide molecule. The amplification of polynucleotides can be carried out in vitro by biochemical processes known to those of skill in the art. The amplification agent may be any compound or system that will function to accomplish the synthesis of primer extension products, including enzymes. Suitable enzymes for this purpose include, for example, *E. coli* DNA polymerase I, Taq polymerase, Klenow fragment of *E. Coli* DNA polymerase I, T4 DNA polymerase, other available DNA polymerases, polymerase muteins, reverse transcriptase, ligase, and other enzymes, including heat-stable enzymes (i.e., those enzymes that perform primer extension after being subjected to temperatures sufficiently elevated to cause denaturation). Suitable enzymes will facilitate combination of the nucleotides in the proper manner to form the primer extension products that are complementary to each mutant nucleotide strand. Generally, the synthesis will be initiated at the 3' end of each primer and proceed in the 5' direction along the template strand, until synthesis terminates, producing molecules of different lengths. There may be amplification agents, however, that initiate synthesis at the 5' end and proceed in the other direction, using the same process as described above. In any event, the method of the invention is not to be limited to the embodiments of amplification described herein.

One method of in vitro amplification which can be used according to this invention is the polymerase chain reaction (PCR) described in U.S. Pat. Nos. 4,683,202 and 4,683,195. The term "polymerase chain reaction" refers to a method for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. The polymerase chain reaction is used to detect the presence of polynucleotides encoding cytokines in the sample. Many polymerase chain methods are known to those of skill in the art and may be used in the method of the invention. For example, DNA can be subjected to 30 to 35 cycles of amplification in a thermocycler as follows: 95° C. for 30 sec, 52° to 60° C. for 1 min, and 72° C. for 1 min, with a final extension step of 72° C. for 5 min. For another example, DNA can be subjected to 35 polymerase chain reaction cycles in a thermocycler at a denaturing temperature of 95° C. for 30 sec, followed by varying annealing temperatures ranging from 54–58° C. for 1 min, an extension step at 70° C. for 1 min and a final extension step at 70° C.

The primers for use in amplifying the polynucleotides of the invention may be prepared using any suitable method, such as conventional phosphotriester and phosphodiester methods or automated embodiments thereof so long as the primers are capable of hybridizing to the polynucleotides of interest. One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the method of the invention are complementary to each strand of nucleotide sequence to be amplified. The term "complementary" means that the primers must hybridize with their respective strands under conditions which allow the agent for polymerization to function. In other words, the primers that are complementary to the flanking sequences hybridize with the flanking sequences and permit amplification of the nucleotide sequence. Preferably, the 3' terminus of the primer that is extended has perfectly base paired complementary with the complementary flanking strand.

Those of ordinary skill in the art will know of various amplification methodologies which can also be utilized to increase the copy number of target nucleic acid. The polynucleotides detected in the method of the invention can be further evaluated, detected, cloned, sequenced, and the like, either in solution or after binding to a solid support, by any method usually applied to the detection of a specific nucleic acid sequence such as another polymerase chain reaction, oligomer restriction (Saiki et al., *Bio/Technology* 3: 1008–1012 (1985)), allele-specific oligonucleotide (ASO) probe analysis (Conner et al., *Proc. Natl. Acad. Sci. USA* 80: 278 (1983), oligonucleotide ligation assays (OLAs) (Landegren et al, *Science* 241: 1077 (1988)), RNAse Protection Assay and the like. Molecular techniques for DNA analysis have been reviewed (Landegren et al, *Science,* 242: 229–237 (1988)). Following DNA amplification, the reaction product may be detected by Southern blot analysis, without using radioactive probes. In such a process, for example, a small sample of DNA containing the polynucleotides obtained from the tissue or subject are amplified, and analyzed via a Southern blotting technique. The use of non-radioactive probes or labels is facilitated by the high level of the amplified signal. In one embodiment of the invention, one nucleoside triphosphate is radioactively labeled, thereby allowing direct visualization of the amplification product by autoradiography. In another embodiment, amplification primers are fluorescently labeled and run through an electrophoresis system. Visualization of amplified products is by laser detection followed by computer assisted graphic display.

Simple visualization of a gel containing the separated products may be utilized to determine the presence or expression of PINCH. For example, staining of a gel to visualize separated polynucleotides, a number of stains are well known to those skilled in the art. However, other methods known to those skilled in the art may also be used, for example scanning densitometry, computer aided scanning and quantitation as well as others.

Another technique which may be used to detect PINCH or ILK involves the use of antibodies. Such antibodies may consist of an antibody coupled to a low molecular weight hapten. These haptens can then be specifically detected by means of a second reaction. For example, it is common to use such haptens as biotin, which reacts with avidin, or dinitrophenyl, pyridoxal, and fluorescein, which can react with specific antihapten antibodies.

The method for detecting a cell expressing PINCH or a cell proliferative disorder associated with PINCH, described above, can be utilized for detection of breast cancer or other malignancies in a subject, including those in a state of clinical remission. Additionally, the method for detecting PINCH polypeptide in cells is useful for detecting a cell proliferative disorder by measuring the level of PINCH in cells or in a suspect tissue in comparison with PINCH expressed in a normal or standard cell or tissue. Using the method of the invention, PINCH expression can be identified in a cell and the appropriate course of treatment can be employed (e.g., antisense gene therapy or drug therapy). The expression pattern of PINCH may vary with the stage of malignancy of a cell, therefore, a sample such as breast tissue can be screened with a panel of PINCH-specific reagents (i.e., nucleic acid probes or antibodies to PINCH) to detect PINCH expression and diagnose the stage of malignancy of the cell. Additionally, the inventors have discovered that expression of ILK is related to cell proliferative disorders. Thus, as discussed more fully below, expression of ILK is indicative of a metastatic cell proliferative disorder. In this regard, the sample may also be screened with polynucleotides to ILK or antibodies to an ILK polypeptide, wherein detection of over-expressed ILK and PINCH would be indicative of a metastatic cell proliferative disorder. Polynucleotide probes to ILK can be developed using techniques well known in the art. For example, a complementary polynucloeotide strand to an ILK polynucleotide can be used as a probe in Northern and Southern blots. Additionally, an oligonucleotide complementary to an ILK polynucleotide can also be used as a probe or as a primer for PCR amplification of ILK. Finally, antibodies can be used to detect expression of ILK polypeptides. The antibodies may be monoclonal or polyclonal.

Monoclonal antibodies used in the method of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay.

Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of PINCH and/or ILK. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

For purposes of the invention, PINCH and/or ILK may be detected by the monoclonal antibodies when present in biological fluids and tissues. Any sample containing a detectable amount of PINCH or ILK can be used. A sample can be a liquid such as blood, serum and the like, or a solid or semi-solid such as tissues, feces, and the like, or, alternatively, a solid tissue such as those commonly used in histological diagnosis.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-PINCH immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i. e., nonspecific) antibodies of the same class or subclass (isotype) as those used in the assays (e.g., IgG1, IgG2a, IgM, etc.) can be used as "blockers". The concentration of the "blockers" (normally 1–100 $\mu g/\mu l$) may be important, in order to maintain the proper sensitivity yet inhibit any unwanted interference by mutually occurring cross reactive proteins in the specimen.

In Vivo Diagnostics

Monoclonal antibodies may be used for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the PINCH or ILK antigen for which the monoclonal antibodies are specific.

The concentration of detectably labeled monoclonal antibody which is administered should be sufficient such that the binding to those cells having PINCH or ILK is detectable compared to the background. Further, it is desirable that the detectably labeled monoclonal antibody be rapidly cleared from the circulatory system in order to give the best target-to-background signal ratio. Typically, the monoclonal antibody is readioactively labelled, however, other labels are within the scope of the invention, for example, paramagnetic isotopes.

Additionally, monoclonal antibodies to ILK may be administered alone or simultaneously with PINCH.

As a general rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

A monoclonal antibody useful in the method of the invention can also be labeled with a para-magnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

Monoclonal antibodies used in the method of the invention can be used to monitor the course of amelioration of PINCH associated cell proliferative disorder. Thus, by measuring the increase or decrease in the number of cells expressing PINCH or changes in PINCH present in various body fluids, such as blood or serum, it would be possible to determine whether a particular therapeutic regiment aimed at ameliorating the disorder is effective.

Therapeutic Techniques

The present invention also provides a method for treating a subject with PINCH-associated cell proliferative disorder. For example, in breast cancer, the PINCH nucleotide sequence is over-expressed in a cell as compared to expression in a normal-standard cell, therefore, it is possible to design appropriate therapeutic or diagnostic techniques directed to this sequence. Thus, where a cell-proliferative disorder is associated with the expression of PINCH, polynucleotide sequences that modulate Pinch expression at the transcriptional or translational level can be used. In cases when a cell proliferative disorder or abnormal cell phenotype is associated with the under expression of PINCH, for example, nucleic acid sequences encoding PINCH (sense) could be administered to the subject with the disorder. In cases when a cell proliferative disorder, such as those seen in a breast caner, is associated with the over-expression of PINCH an antisense or ribozyme therapy may be appropriate.

The term "cell-proliferative disorder" denotes malignant as well as non-malignant cell populations which often appear to differ from the surrounding tissue both morphologically and genotypically. Such disorders may be associated, for example, with over- expression of PINCH, ILK or a combination thereof. Essentially, any disorder which is etiologically linked to expression of PINCH could be considered susceptible to treatment with a reagent of the invention which modulates PINCH expression.

The term "modulate" or "regulates" envisions the augmentation of PINCH activity or PINCH gene expression. When a cell proliferative disorder is associated with PINCH expression, antibodies which bind PINCH may prevent PINCH activity. Similarly, antisense oligonucleotides may bind to DNA or RNA encoding PINCH and thus prevent its expression.

Antisense oligonucleotides can effectively reduce PINCH expression and can be used to treat disease associated with PINCH, such as signal transduction disorders, including cell proliferative disorders, neoplasms, or cancer, for example breast cancer. The antisense oligonucleotides can be delivered to cells in culture or to cells or tissues in humans or delivered in animal models having these diseases. Binding of PINCH polynucleotide by an antisense oligonucleotide can be used to inhibit cell proliferation associated with cell proliferative disorders. Furthermore, when used in combination with antisense oligonucleotides to ILK, the combination therapy can be used to inhibit metastatic cell proliferative disorders.

"Antisense oligonucleotide" means any RNA or DNA molecules which can bind specifically with a targeted polynucleotide sequence, interrupting the expression of that gene's protein product. The antisense molecule binds to either the messenger RNA forming a double stranded molecule which cannot be translated by the cell or to the DNA or other polynucleotide encoding PINCH or ILK. Antisense oligonucleotides of about 8 to 40 nucleic acids and more preferably about 13–30 are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. These and other uses of antisense methods to inhibit the in vitro translation of genes are well known in the art (Marcus-Sakura, 1988, *Anal., Biochem.*, 172:289).

Antisense oligonucleotides are DNA or RNA molecules that are complementary to, at least a portion of, a specific polynucleotide molecule (Weintraub, *Scientific American*, 262:40, 1990). In the cell, the antisense oligonucleotides hybridize to the corresponding target polynucleotide, forming a double-stranded or triplex molecule. The antisense oligonucleotides interfere with the translation of, for example, mRNA, since the cell will not translate a mRNA that is double-stranded. Antisense oligomers of about 8 to 40 nucleotides are preferred, since they are easily synthesized and are less likely to cause problems than larger molecules when introduced into the target PINCH producing cell.

Use of a oligonucleotides to stall transcription is known as the triplex strategy since the oligomer winds around double-helical DNA, forming a three-strand helix. Therefore, these triplex compounds can be designed to recognize a unique site on a chosen gene (Maher, et al., 1991, *Antisense Res. and Dev.*, 1(3):227; Helene, C., 1991, *Anticancer Drug Design*, 6(6):569).

These and other uses of antisense methods to inhibit the in vivo transcription or translation of genes are well known in the art (e.g., De Mesmaeker, et al., 1995. Backbone modifications in oligonucleotides and peptide nucleic acid systems. *Curr. Opin. Struct. Biol.* 5:343–355; Gewirtz, A. M., et al., 1996b. Facilitating delivery of antisense oligodeoxynucleotides: Helping antisense deliver on its promise; *Proc. Natl. Acad. Sci. U.S.A.* 93:3161–3163; Stein, C. A. A discussion of G-tetrads 1996. Exploiting the potential of antisense: beyond phosphorothioate oligodeoxynucleotides. *Chem. and Biol.* 3:319–323).

The invention includes antisense oligonucleotides which hybridize with a polynucleotide sequence comprising SEQ ID NO:1 or its complement. The antisense oligonucleotides employed may be unmodified or modified RNA or DNA molecules. Suitable modifications include, but are not limited to, the ethyl or methyl phosphorate modification disclosed in U.S. Pat. No. 4,469,863, the disclosure of which is incorporated by reference, and the phosphorothioate modifications to deoxynucleotides described by LaPlanche, et al., 1986 *Nucleic Acids Research*, 14:9081, and by Stec, et al., 1984 *J. Am. Chem Soc.* 106:6077. The modification to the antisense oligonucleotides is preferably a terminal modification in the 5' or 3' region. Preferred are modifications of the 3' terminal region. Also preferred are modifications with methyl groups added to 5' carbon atoms as described by Saha, et al., 1993 *CEN*, 44:44.

Phosphodiester-linked oligonucleotides are particularly susceptible to the action of nucleases in serum or inside cells, and therefore in a preferred embodiment the antisense molecules of the present invention are phosphorothioate or methyl phosphonate-linked analogues, which have been shown to be nuclease-resistant. Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2NHOCH_2$, $CH_2N(CH_3)OCH_2$, $CH_2ON(CH_3)CH_2$, $CH_2N(CH_3)N(CH_3)CH_2$ and $ON(CH_3)$ $CH_2CH_2$ backbones (where phosphodiester is $OPOCH_2$). Also preferred are oligonucleotides having morpholino backbone structures (Summerton, J. E. and Weller, D. D., U.S. Pat. No. 5,034,506). In other preferred embodiments, 2'-methylribonucleotides (Inoue, et al., 1987 *Nucleic Acids Research*, 15:6131) and chimeric oligonucleotides that are composite RNA-DNA analogues (Inoue, et al., 1987 *FEBS Lett.*, 215:327) may also be used for the purposes described herein. Finally, DNA analogues, such as peptide nucleic acids (PNA) are also included (Egholm, et al., 1993 *Nature* 365:566; P. E. Nielsen, M. Egholm, R. H. Berg, O. Buchardt, 1991 *Science*, 254:1497) and can be used according to the invention. Other preferred oligonucleotides may contain alkyl and halogen-substituted sugar moieties comprising one of the following at the 2' position: OH, SH, $SCH_3$, F, OCN, $OCH_3OCH_3$, $OCH_3O(CH_2)nCH_3$, $O(CH_2)nNH_2$ or $O(CH_2)$ $nCH3$ where n is from 1 to about 10; C1 to C10 lower alkyl, substituted lower alkyl, alkaryl or aralkyl; Cl; Br; CN; $CF_3$; $OCF_3$; O, S , or N-alkyl; O, S or N alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a conjugate; a reporter group; an intercalator; a group for improving the pharmacokinetic properties of a oligonucleotide; or a group for improving the pharmacodynamic properties of a oligonucleotide and other substituents having similar properties. Oligonucleotides may also have sugar mimetics such as cyclobutyls in place of the pentofuranosyl group. Other preferred embodiments may include at least one modified base form or "universal base" such as inosine. The preparation of base-modified nucleosides, and the synthesis of modified oligonucleotides using said base-modified nucleosides as precursors, has been described, for example, in U.S. Pat. Nos. 4,948,882 and 5,093,232. These base-modified nucleosides have been designed so that they can be incorporated by chemical synthesis into either terminal or internal positions of a oligonucleotide. Such base-modified nucleosides, present at either terminal or internal positions of a oligonucleotide, can serve as sites for attachment of a peptide or other antigen. Nucleosides modified in their sugar moiety have also been described (e.g., U.S. Pat. No. 5,118, 802) and can be used similarly. Persons of ordinary skill in this art will be able to select other linkages for use in the invention. These modifications also may be designed to improve the cellular uptake and stability of the oligonucleotides. It is understood that depending on the route or form of administration of the antisense oligonucleotides of the invention, the modification or site of modification will vary (e.g., 5' or 3' modification). One of skill in the art could readily determine the appropriate modification without undue experimentation.

In order for the target cell, tissue or subject to be rendered susceptible to the antisense oligonucleotides in accordance with the method of the invention, the cells must be exposed to the oligonucleotide under condition that facilitate their uptake by the cell, tissue or subject. In vitro therapy may be accomplished by a number of procedures, including, for example, simple incubation of the cells or tissue with the oligonucleotide in a suitable nutrient medium for a period of time suitable to inhibit PINCH production.

The antisense oligonucleotides of the invention can be delivered alone or in conjunction with other agents such as immunosuppressive drugs, ribozymes or other antisense molecules. For example, ribozymes or antisense molecules that specifically bind mRNA encoding ILK, or a cytokine, such as TNF-α or interferon-γ, can be used with the antisense molecules of the present invention.

Additionally, the antisense oligonucleotides of the present invention may be administered ex vivo by harvesting cells or tissue from a subject, treating them with the antisense oligonucleotide, then returning the treated cells or tissue to the subject. The present invention provides method for the treatment of a disease which is associated with PINCH. Such therapy would achieve its therapeutic effect by introduction of the appropriate antisense oligonucleotide which binds polynucleotides encoding PINCH into cells of subjects having the disorder. Delivery of the PINCH antisense molecule can be achieved using a recombinant expression vector such as a chimeric virus or a colloidal dispersion system.

Many of the methods as described herein can be performed in vivo or ex vivo. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a sequence encoding an antisense oligonucleotide which specifically binds polynucleotides encoding PINCH into the viral vector, along with another gene which encodes the ligand for a receptor on a specific target cell, for example, the vector is now target specific. Preferred targeting is accomplished by using an antibody to target the retroviral vector. Those of skill in the art will know of, or can readily ascertain without undue experimentation, specific polynucleotide sequences which can be inserted into the retroviral genome, for example, to allow target specific delivery of the retroviral vector containing the antisense oligonucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for antisense oligonucleotides that bind polynucleotides encoding PINCH is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., 1981 *Trends Biochem. Sci.*, 6:77). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., 1988 *Biotechniques*, 6:682).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

Another delivery system for the antisense oligonucleotides of the invention at particular sites in a subject, includes the use of gene-activated matrices. In this system the antisense molecule is coated on a biocompatible matrix, sponge or scaffold and implanted at the tissue site wherein cells proliferate and grow on the scaffold, taking up the antisense oligonucleotide (See for example U.S. Pat. No. 5,763,416, which is incorporated herein by reference).

In yet another delivery system, the antisense molecules of the invention may be microinjected into cells. The antisense molecules may be prepared in an appropriate buffer and the naked oligonucleotide, either alone or contained in an appropriate vector, microinjected, for example, into a stem cell of a tissue to be treated.

In addition, antisense oligonucleotides according to the invention may also be administered in vivo. Antisense oligonucleotides can be administered as a compound or as a pharmaceutically acceptable salt of the compound, alone or in combination with pharmaceutically acceptable carriers, diluents, simple buffers, and vehicles. For example, expression vectors that produce antisense molecules can be engineered from DNA duplexes in the laboratory and introduced into cells (Weintraub, et al., 1990 *Sci. Amer.* 1:40). Most preferably, antisense oligonucleotides are mixed individually or in combination with pharmaceutically acceptable carriers to form compositions which allow for easy dosage preparation.

An antisense oligonucleotide of the invention can be administered to provide in vivo therapy to a subject having a disorder which is associate with PINCH expression. Such therapy can be accomplished by administering ex vivo and in vivo as the case may be, a therapeutically effective amount of antisense oligonucleotide. The term "therapeutically effective" means that the amount of antisense oligonucleotide administered is of sufficient quantity to suppress, to some beneficial degree, expression of PINCH.

Antisense oligonucleotide according to the present invention can be administered to the patient in any acceptable manner including orally, by injection, using an implant, nasally and the like. Oral administration includes administering an oligonucleotide of the present invention in tablets, suspension, implants, solutions, emulsions, capsules, powders, syrups, water composition, and the like. Nasal administration includes administering the composition of the present invention in sprays, solutions and the like. Injections and implants are preferred because they permit precise control of the timing and dosage levels useful for administration, with injections being most preferred. Antisense oligonucleotides are preferably administered parenterally.

The therapeutic agents useful in the method of the invention can be administered parenterally by injection or by gradual profusion over time. Administration may be intravenously, intra-peritoneally, intramuscularly, subcutaneously, intra-cavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

The invention also includes a composition for therapy comprising an effective amount of an enzymatic RNA of the invention or combination thereof, and a physiologically acceptable excipient or carrier.

Physiologically acceptable and pharmaceutically acceptable excipients and carriers are well known to those of skill in the art. By "physiologically or pharmaceutically acceptable carrier" as used herein is meant any substantially non-toxic carrier for administration in which an antisense oligonucleotide of the invention will remain stable and bioavailable when used. For example, the antisense oligonucleotide of the invention can be dissolved in a liquid, dispersed or emulsified in a medium in a conventional manner to form a liquid preparation or is mixed with a semi-solid (gel) or solid carrier to form a paste, ointment, cream, lotion or the like.

Suitable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, or gum arabic, synthetic polymers, such as discussed below, alcohols, polyols, water and the like. Preferably, because of its non-toxic properties, the carrier is a water miscible carrier composition that is substantially miscible in water. Such water miscible carrier composition can include those made with one or more ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions or gels.

The carrier can comprise a sustained release or delayed release carrier. The carrier is any material capable of sustained or delayed release of the antisense molecule specifically directed against PINCH polynucleotide to provide a more efficient administration resulting in one or more of less frequent and/or decreased dosage of the antisense molecule, ease of handling, and extended or delayed effects. The carrier is capable of releasing the oligomer when exposed to the environment of the area for diagnosis or treatment or by diffusing or by release dependent on the degree of loading of the oligonucleotide to the carrier in order to obtain release of the antisense oligonucleotide of the invention. Non-limiting examples of such carriers include liposomes, microsponges, microspheres, gene-activated matrices, as described above, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like.

Preferably, the sustained or delayed release carrier is a liposome, microsponge, microsphere or gel.

The compositions of the invention are administered by any suitable means, including injection, implantation, transdermal, intraocular, transmucosal, bucal, intrapulmonary, and oral.

Preferably the carrier is a pH balanced buffered aqueous solution for injection. However, the preferred carrier will vary with the mode of administration. The compositions for administration usually contain from about 0.0001% to about 90% by weight of the antisense oligonucleotide of the invention compared to the total weight of the composition, preferably from about 0.5% to about 20% by weight of the antisense oligonucleotide of the invention compared to the total composition, and especially from about 2% to about 20% by weight of the antisense oligonucleotide of the invention compared to the total composition.

The effective amount of the antisense oligonucleotide of the invention used for therapy or diagnosis of course can vary depending on one or more of factors such as the age and weight of the patient, the type of formulation and carrier ingredients, frequency of use, the type of therapy or diagnosis preformed and the like. It is a simple matter for those of skill in the art to determine the precise amounts to use taking into consideration these factors and the present specification.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting PINCH antibody-containing liposomes directly to the malignant tumor. Since the PINCH gene product may be indiscriminate with respect to cell type in its action, a targeted delivery system offers a significant improvement over randomly injecting non-specific liposomes. Preferably, the target tissue is a breast tissue. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an the antigenic epitope on the target cells. Liposomes may also be targeted to cells expressing receptors for hormones or other serum factors.

Pinch Regulating and Blocking Agents

In yet another embodiment, the present invention relates to PINCH-binding and/or blocking agents. Such agents could represent research and diagnostic tools in the study of cell proliferative disorders. In addition, pharmaceutical compositions comprising isolated and purified PINCH-binding agents may represent effective cancer therapeutics. The phrase "PINCH-binding agent" denotes an agents which functions to bind PINCH polypeptide or the promotor region of the PINCH gene. The term includes both biologic agents and chemical compounds. The determination and isolation of ligand/compositions is well described in the art. See, e.g. Lerner, *Trends NeuroSci.* 17:142–146 (1994), which is hereby incorporated in its entirety by reference.

Screening for Pinch Binding Compounds

Also included is a method of identifying compounds that bind PINCH polypeptide or fragments thereof. The method for identifying a compound which binds to PINCH polypeptide comprises incubating a test compound and PINCH polypeptide under conditions sufficient to allow the compound and PINCH polypeptide to form a complex. Conditions will vary according to a number of factors well recognized in the art, including temperature, concentration, hydrophobicity and hydrophilicity of the molecules, for example hydrophobic molecules such as long chain fatty acids may require buffers including dimethylsulfoxide (DMSO). Compounds can thus be any number of molecules including polypeptides, peptidomimetics, carbohydrates, fatty acids, and/or steroids. The molecules may be labeled. For example the PINCH or the test compound may be chemically labeled with a fluorescence compound, a radioactive element or a metal chelating agent. The method also involves separating a complex of PINCH polypeptide and the binding compound from unbound PINCH polypeptide and measuring the binding or effect of binding of the compound to PINCH polypeptide. Separation of the compounds and PINCH can be accomplished by any number of means including chromatography, gel electrophoresis and other well known to those skilled in the art.

EXAMPLE

Antibodies and anti-sera were prepared by creating a 6-histidine PINCH fusion protein by ligation of a PCR product containing the entire human PINCH open reading frame in-frame with the pAcSG His NT baculovirus transfer vector (PharMingen), which was then co-transfected with BACULOGOLD DNA (a modified baculovirus DNA) into insect cells. Recombinant PINCH was purified by chromatography of insect cell lysates on a metal chelate matrix (ProBond, Invitrogen). Rabbits were immunized with recombinant PINCH isolated from SDS-polyacrylamide gels, and antisera produced at Rackland Laboratories, Gilbertsville, Pa. Rabbit anti-PINCH IgG was affinity-purified using a GST fusion protein corresponding to the third PINCH LIM domain and used at 1 ug/ml. Rabbit anti-ILK (Upstate Biotechnology) was used at 1 ug/ml, mouse anti-cylni D1 (Santa Cruz) was used at 0.2 ug/ml, and mouse anti-erbB-2 (NovoCastra) was used at 1:500.

To determine whether PINCH and ILK had affects in cell proliferative disorders associated with cell signaling, excess pathological material was obtained from the Clinical Laboratory of the University of California, San Diego Medical Center-Thorton Hospital according to guidelines established by the institutional review committee. The tissues were solubilized in RIPA buffer (50 mM sodium borate, 150 mM NaCl, 1% Nonidet P-40, 0.5% sodium deoxycholate) containing protease inhibitors (0.1 mg/ml phenylmethylsulfonyl fluoride, 1 ug/ml aprotinin and 1 ug/ml leupeptin). Protein concentration of the tissue lysates were determined by the dotMETRIC assay (Chemicon International) following the manufacturer's instructions and confirmed by Comassie blue staining of SDS-polyacrylamide gels.

Solubilized breast proteins were boiled in loading buffer containing 200 mM dithiothreitol and 720 mM 2-mercaptoethanol for 5 minutes, separated by electrophoresis on SDS-polyacrylamide gels and transferred to nitrocellulose (Hybond-ECL, Amersham) in transfer buffer (25 mM ethanolamine/glycine, pH 9.5, containing 20% methanol). Immunoblots were blocked with 5% blocking agent (Amersham) in Tris-buffered saline, pH 7.5 (TBS) and reacted overnight at 4° C. with antibody in TBS with 1% blocking agent. Following washing in TBS/0.1% Tween-20, immunoblots were reacted for 30 minutes with the appropriate horseradish peroxidase-conjugated anti-rabbit or anti-mouse Ig (Amersham). Reactions were detected by enhanced chemiluminescence (ECL detection kit, Amersham). To estimate the magnitude of specific protein increases in breast cancer, a known quantity of normal breast tissue lysate was compared on immunoblots to the same quantity of breast cancer tissue lysate, as well as to 1/3 and 1/6 quantities of breast cancer tissue lysate. Anti-cyclin D1 staining showed high sensitivity, detecting cyclin D1 in all samples including the normals, and therefore cyclin D1 was determined to be increased when it could clearly be detected at 1/3 quantity.

Using the techniques described, the cases examined represented a spectrum of breast cancer diagnoses, and varied in expression of known prognostic indicators: 4/6 breast cancer cases were positive for cyclin D1, 3/6 were positive for erbB-2 (HER2/neu), and ⅔ were positive for estrogen and progesterone receptors (FIG. 1). The greatest increase in PINCH and ILK was found in cases of metastatic breast carcinoma (case 7, FIG. 1) which was positive for cyclin D1 and erbB-2 and negative for estrogen and progesterone receptors. The most modest increase in PINCH and ILK was found in a low-risk breast cancer case (case 3, FIG. 1) which in contrast to case 7, was negative for cyclin D1 and erbB-2 and positive for estrogen and progesterone receptors. Thus, the study demonstrates that the adapter protein PINCH and its associated serine-threonine kinase ILK are significantly increased over normal in a sample of breast cancer tissue lysates. All six breast cancer tissue lysates showed increased PINCH and ILK, suggesting that upregulation of the PINCH signaling complex may be an early event in breast cancer. Furthermore, case #3 was a small, localized lesion that was shown by DNA analysis to be euploid and to have a low S phase fraction, while case #7 was an aggressive metastatic lesion. These results support the finding that ILK overexpression is important in determining cell phenotype, and that the higher the level of ILK overexpression, the more aggressive and invasive the tumor.

A number of embodiments of the present invention have been described. Nevertheless, it will be understood that various modifications may be made without departing from the spirit and scope of the invention. Accordingly, other embodiments are within the scope of the following claims.

What is claimed is:

1. A method of diagnosing a cell proliferative disorder in a subject associated with PINCH having the amino acid sequence set forth in SEQ ID NO:2, comprising:

determining the level of PINCH in the sample; and comparing the level of PINCH in the sample to the level of PINCH in a standard sample, wherein an elevated level of PINCH in the sample is indicative of a cell proliferative disorder.

2. The method of claim 1, wherein the cell proliferative disorder is a neoplasm.

3. The method of claim 2, wherein the neoplasm is breast neoplasm.

4. The method of claim 1, further comprising determining the level of integrin-linked kinase (ILK).

5. The method of claim 4, wherein an elevated level of ILK compared to a standard sample is indicative of a metastatic cell proliferative disorder.

6. A method of diagnosing breast cancer in a subject comprising:

detecting an elevated amount of PINCH having the amino acid sequence set forth in SEQ ID NO:2 in cells isolated from the subject, wherein an elevated amount of PINCH in comparison to the level of PINCH in a standard sample is indicative of breast cancer.

7. The method of claim 6, wherein the elevated amounts of PINCH are determined by detecting a nucleic acid encoding PINCH.

8. The method of claim 6, wherein the subject is a mammal.

* * * * *

SEQUENCE LISTING

```
<160> NUMBER OF SEQ ID NOS:  2

<210> SEQ ID NO 1
<211> LENGTH: 1246
<212> TYPE: DNA
<213> ORGANISM: Homo sapiens
<220> FEATURE:
<221> NAME/KEY: CDS
<222> LOCATION: (120)...(1061)

<400> SEQUENCE: 1
tagttcaaga caacagagac aaagctaaga tgaggaagtt ctgtacagtt taggaaatag          60
aggctttcaa agataattcg cagtgatgtg aaactggcct cccaagccct gataacaac         119 atg gcc aac gcc ctg gcc agc gcc act tgc gag cgc tgc aag ggc ggc         167
Met Ala Asn Ala Leu Ala Ser Ala Thr Cys Glu Arg Cys Lys Gly Gly
  1               5                  10                  15 ttt gcg ccc gct gag aag atc gtg aac agt aat ggg gag ctg tac cat         215
Phe Ala Pro Ala Glu Lys Ile Val Asn Ser Asn Gly Glu Leu Tyr His
             20                  25                  30 gag cag tgt ttc gtg tgc gct cag tgc ttc cag cag ttc cca gaa gga         263
Glu Gln Cys Phe Val Cys Ala Gln Cys Phe Gln Gln Phe Pro Glu Gly
         35                  40                  45 ctc ttc tat gag ttt gaa gga aga aag tac tgt gaa cat gac ttt cag         311
Leu Phe Tyr Glu Phe Glu Gly Arg Lys Tyr Cys Glu His Asp Phe Gln
     50                  55                  60 atg ctc ttt gcc cct tgc tgt cat cag tgt ggt gaa ttc atc att ggc         359
Met Leu Phe Ala Pro Cys Cys His Gln Cys Gly Glu Phe Ile Ile Gly
 65                  70                  75                  80 cga gtt atc aaa gcc atg aat aac agc tgg cat ccg gag tgc ttc cgc         407
Arg Val Ile Lys Ala Met Asn Asn Ser Trp His Pro Glu Cys Phe Arg
                 85                  90                  95 tgt gac ctc tgc cag gaa gtt ctg gca gat atc ggg ttt gtc aag aat         455
Cys Asp Leu Cys Gln Glu Val Leu Ala Asp Ile Gly Phe Val Lys Asn
            100                 105                 110 gct ggg aga cac ctg tgt cgc ccc tgt cat aat cgt gag aaa gcc aga         503
Ala Gly Arg His Leu Cys Arg Pro Cys His Asn Arg Glu Lys Ala Arg
        115                 120                 125 ggc ctt ggg aaa tac atc tgc cag aaa tgc cat gct atc atc gat gag         551
Gly Leu Gly Lys Tyr Ile Cys Gln Lys Cys His Ala Ile Ile Asp Glu
    130                 135                 140 cag cct ctg ata ttc aag aac gac ccc tac cat cca gac cat ttc aac         599
Gln Pro Leu Ile Phe Lys Asn Asp Pro Tyr His Pro Asp His Phe Asn
145                 150                 155                 160 tgc gcc aac tgc ggg aag gag ctg act gcc gat gca cgg gag ctg aaa         647
```

```
Cys Ala Asn Cys Gly Lys Glu Leu Thr Ala Asp Ala Arg Glu Leu Lys
                165                 170                 175 ggg gag cta tac tgc ctc cca tgc cat gat aaa atg ggg gtc ccc atc     695
Gly Glu Leu Tyr Cys Leu Pro Cys His Asp Lys Met Gly Val Pro Ile
            180                 185                 190 tgt ggt gct tgc cga cgg ccc atc gaa ggg cgc gtg gtg aac gct atg     743
Cys Gly Ala Cys Arg Arg Pro Ile Glu Gly Arg Val Val Asn Ala Met
        195                 200                 205 ggc aag cag tgg cat gtg gag cat ttt gtt tgt gcc aag tgt gag aaa     791
Gly Lys Gln Trp His Val Glu His Phe Val Cys Ala Lys Cys Glu Lys
    210                 215                 220 ccc ttt ctt gga cat cgc cat tat gag agg aaa ggc ctg gca tat tgt     839
Pro Phe Leu Gly His Arg His Tyr Glu Arg Lys Gly Leu Ala Tyr Cys
225                 230                 235                 240 gaa act cac tat aac cag cta ttt ggt gat gtt tgc ttc cac tgc aat     887
Glu Thr His Tyr Asn Gln Leu Phe Gly Asp Val Cys Phe His Cys Asn
                245                 250                 255 cgt gtt ata gaa ggt gat gtg gtc tct gct ctt aat aag gcc tgg tgc     935
Arg Val Ile Glu Gly Asp Val Val Ser Ala Leu Asn Lys Ala Trp Cys
            260                 265                 270 gtg aac tgc ttt gcc tgt tct acc tgc aac act aaa tta aca ctc aag     983
Val Asn Cys Phe Ala Cys Ser Thr Cys Asn Thr Lys Leu Thr Leu Lys
        275                 280                 285 aat aag ttt gtg gag ttt gac atg aag cca gtc tgt aag aag tgc tat    1031
Asn Lys Phe Val Glu Phe Asp Met Lys Pro Val Cys Lys Lys Cys Tyr
    290                 295                 300 gag att tcc att gga gct gaa gaa aag act taagaaacta gctgagacct      1081
Glu Ile Ser Ile Gly Ala Glu Glu Lys Thr
305                 310 taggaaggaa ataagttcct ttatttttc ttttctatgc aagataagag attaccaaca   1141
ttacttgtct tgatctaccc atatttaaag ctatatctca aagcagttga gagaagagga  1201
cctatatgaa tggttttatg tcattttttt aaaaaaaaaa aaaaa                  1246

<210> SEQ ID NO 2
<211> LENGTH: 314
<212> TYPE: PRT
<213> ORGANISM: Homo sapiens

<400> SEQUENCE: 2

Met Ala Asn Ala Leu Ala Ser Ala Thr Cys Glu Arg Cys Lys Gly Gly
1               5                   10                  15

Phe Ala Pro Ala Glu Lys Ile Val Asn Ser Asn Gly Glu Leu Tyr His
                20                  25                  30

Glu Gln Cys Phe Val Cys Ala Gln Cys Phe Gln Gln Phe Pro Glu Gly
            35                  40                  45

Leu Phe Tyr Glu Phe Glu Gly Arg Lys Tyr Cys Glu His Asp Phe Gln
    50                  55                  60

Met Leu Phe Ala Pro Cys Cys His Gln Cys Gly Glu Phe Ile Ile Gly
65                  70                  75                  80

Arg Val Ile Lys Ala Met Asn Asn Ser Trp His Pro Glu Cys Phe Arg
                85                  90                  95

Cys Asp Leu Cys Gln Glu Val Leu Ala Asp Ile Gly Phe Val Lys Asn
            100                 105                 110

Ala Gly Arg His Leu Cys Arg Pro Cys His Asn Arg Glu Lys Ala Arg
        115                 120                 125

Gly Leu Gly Lys Tyr Ile Cys Gln Lys Cys His Ala Ile Ile Asp Glu
    130                 135                 140
```

```
Gln Pro Leu Ile Phe Lys Asn Asp Pro Tyr His Pro Asp His Phe Asn
145                 150                 155                 160

Cys Ala Asn Cys Gly Lys Glu Leu Thr Ala Asp Ala Arg Glu Leu Lys
            165                 170                 175

Gly Glu Leu Tyr Cys Leu Pro Cys His Asp Lys Met Gly Val Pro Ile
            180                 185                 190

Cys Gly Ala Cys Arg Arg Pro Ile Glu Gly Arg Val Val Asn Ala Met
        195                 200                 205

Gly Lys Gln Trp His Val Glu His Phe Val Cys Ala Lys Cys Glu Lys
    210                 215                 220

Pro Phe Leu Gly His Arg His Tyr Glu Arg Lys Gly Leu Ala Tyr Cys
225                 230                 235                 240

Glu Thr His Tyr Asn Gln Leu Phe Gly Asp Val Cys Phe His Cys Asn
                245                 250                 255

Arg Val Ile Glu Gly Asp Val Val Ser Ala Leu Asn Lys Ala Trp Cys
            260                 265                 270

Val Asn Cys Phe Ala Cys Ser Thr Cys Asn Thr Lys Leu Thr Leu Lys
        275                 280                 285

Asn Lys Phe Val Glu Phe Asp Met Lys Pro Val Cys Lys Lys Cys Tyr
    290                 295                 300

Glu Ile Ser Ile Gly Ala Glu Glu Lys Thr
305                 310
```